United States Patent
Siedler et al.

(10) Patent No.: US 10,131,591 B2
(45) Date of Patent: Nov. 20, 2018

(54) HEAT REDUCTION IN ALKYLATION PROCESS

(71) Applicants: UOP LLC, Des Plaines (IL); Compañia Española de Petroleos, S.A.U., Madrid (ES)

(72) Inventors: Nathan Siedler, Palatine, IL (US); Charles P. Luebke, Mount Prospect, IL (US); Cynthia K. Zimmerman, Palatine, IL (US); Jacques Meunier, Madrid (ES); Leopoldo R. Alcázar, Madrid (ES)

(73) Assignees: UOP, LLC, Des Plaines, IL (US); Compañia Española de Petroleos, S.A.U., Madrid (ES)

( * ) Notice: Subject to any disclaimer, the term of this patent is extended or adjusted under 35 U.S.C. 154(b) by 0 days.

(21) Appl. No.: 15/857,175

(22) Filed: Dec. 28, 2017

(65) Prior Publication Data
US 2018/0179124 A1    Jun. 28, 2018

Related U.S. Application Data (60) Provisional application No. 62/439,583, filed on Dec. 28, 2016.

(51) Int. Cl.
| | | |
|---|---|---|
| C07C 2/66 | (2006.01) | |
| B01D 3/32 | (2006.01) | |
| C07C 5/05 | (2006.01) | |
| C07C 5/333 | (2006.01) | |

(52) U.S. Cl.
CPC ................ C07C 2/66 (2013.01); B01D 3/322 (2013.01); C07C 5/05 (2013.01); C07C 5/333 (2013.01)

(58) Field of Classification Search
CPC ......................... B01D 3/322; C07C 2/64–2/70
See application file for complete search history.

(56) References Cited

U.S. PATENT DOCUMENTS

| | | | | |
|---|---|---|---|---|
| 3,294,856 | A | * 12/1966 | Huckins, Jr. | ............ C07C 15/46 |
| | | | | 585/402 |
| 4,463,205 | A | 7/1984 | Spinner | |
| 4,587,370 | A | * 5/1986 | DeGraff | .................... C07C 2/66 |
| | | | | 203/22 |
| 5,900,518 | A | 5/1999 | Merrill et al. | |
| 6,069,285 | A | 5/2000 | Fritsch et al. | |
| 6,133,492 | A | 10/2000 | Anantaneni | |

(Continued)

OTHER PUBLICATIONS

International Search report and Written Opinion for corresponding PCT application No. PCT/US2017/068819, dated Apr. 5, 2018.

*Primary Examiner* — Philip Y Louie
*Assistant Examiner* — Alyssa L Cepluch
(74) *Attorney, Agent, or Firm* — Greer, Burns & Crain, Ltd.

(57) ABSTRACT

Processes using mid-column reboilers in at least one benzene separation columns to reduce the heat duty in alkylation processes are provided. The feed to the aromatics removal zone may exchange heat in a mid-column reboiler in the benzene separation column in the alkylbenzene separation zone followed by exchanging heat in a mid-column reboiler in the benzene separation column in the aromatics removal zone. This arrangement minimizes the hot oil duty on the reboilers in both benzene separation columns.

20 Claims, 2 Drawing Sheets

(56) References Cited

U.S. PATENT DOCUMENTS

| | | | |
|---|---|---|---|
| 6,479,720 B1 * | 11/2002 | O'Brien | C07C 15/00 208/354 |
| 6,762,334 B1 | 7/2004 | Stewart et al. | |
| 7,642,389 B2 | 1/2010 | Sohn et al. | |
| 7,652,182 B2 | 1/2010 | Sohn et al. | |
| 7,692,055 B2 | 4/2010 | Sohn et al. | |
| 7,897,829 B2 | 3/2011 | Glover et al. | |
| 2011/0306809 A1 * | 12/2011 | Nicholas | C07C 2/66 585/323 |
| 2012/0330076 A1 * | 12/2012 | Smith | C07C 2/66 585/447 |
| 2015/0240187 A1 | 8/2015 | Scheibel et al. | |
| 2015/0336023 A1 | 11/2015 | Dunet et al. | |
| 2016/0009612 A1 | 1/2016 | Riley et al. | |

\* cited by examiner

HEAT REDUCTION IN ALKYLATION PROCESS

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Historically, linear alkylbenzenes have been manufactured commercially using Friedel-Crafts condensation employing catalysts such as aluminum chloride, or by using strong acid catalysts such as hydrogen fluoride, for example, to alkylate benzene with olefins.

In 1995, a solid bed alkylation process, the Detal™ process, using a solid non-corrosive acid catalyst was introduced. The solid bed alkylation process includes a separation column to remove benzene from the alkylbenzenes. The benzene separation column has a large hot oil duty for the reboiler.

Some solid bed alkylation processes include an aromatics removal zone, such as a Pacol Enhancement Process (PEP), in which aromatics are removed from the feed to the alkylation reactor. The aromatics removal zone may include at least one aromatics removal units, and a benzene separation column, which also has a large hot oil duty for the reboiler.

It would be desirable to reduce the utility cost for solid bed alkylation processes by reducing the duty on the reboilers used in separation processes.

Thus, there exists a need for methods of reducing the heat duty in an alkylation process.

SUMMARY OF THE INVENTION

Processes using mid-column reboilers in benzene separation columns to reduce the heat duty in alkylation processes have been developed.

One aspect of the invention is a method of heat integration in a process for producing alkylbenzene. The process involves dehydrogenating an n-paraffin rich stream in a dehydrogenation zone under dehydrogenation conditions to form a first dehydrogenated stream comprising n-paraffins, mono-olefins, di-olefins, and aromatics, the dehydrogenated stream having a first temperature. Heat is removed from at least a portion of the first dehydrogenated stream in a mid-column reboiler in a first benzene separation column to form a second dehydrogenated stream, the portion of the first dehydrogenated stream having a first temperature in a range of about 150° C. to about 250° C., the second dehydrogenated stream having a second temperature lower than the first temperature, the second temperature being in a range of about 135° C. to about 165° C. The aromatics are removed from the second dehydrogenated stream in an aromatics removal zone to form an aromatics stream, a mono-olefin stream, and a first benzene stream, the aromatics removal zone comprising at least one aromatics removal unit and a second benzene separation column. Benzene is alkylated with the mono-olefin stream in an alkylation zone under alkylation conditions to provide an alkylation effluent stream comprising alkylbenzene, benzene, and n-paraffins. The alkylation effluent stream is separated into an alkylbenzene stream and a second benzene stream in an alkylbenzene separation zone comprising the first benzene separation column.

In a preferred method, heat is removed from the second dehydrogenated stream in a mid-column reboiler in the second benzene separation column to form a third dehydrogenated stream having a third temperature lower than the second temperature before removing the aromatics from the second dehydrogenated stream, the mid-column reboiler positioned such that the third temperature being in a arrange of about 110° C. to about 140° C. This process minimizes the hot oil duty on the reboilers in both benzene separation columns.

DETAILED DESCRIPTION OF THE INVENTION

Alkylbenzenes, also known as phenyl alkanes, are important for many different products. When the alkyl group has 8 to 20 carbon atoms, among the common usages is in the formation of detergents. Alkylbenzenes are an intermediate product used to form alkylbenzene sulfonates, which are surfactants that form the basis of many detergents.

Integrated processes for producing LABs using solid alkylation catalysts have been developed which include dehydrogenation, selective catalytic hydrogenation, aromatics removal, and alkylation.

Reduction of the heat duty in the separation processes used in LAB manufacturing processes is accomplished using mid-column reboilers in at least one benzene separation column. Desirably, there are mid-column reboilers in the benzene separation column in the alkylbenzene separation zone and in the aromatics removal zone. Desirably, the feed to the aromatics removal zone exchanges heat in a mid-column reboiler in the benzene separation column in the alkylbenzene separation zone followed by exchanging heat in a mid-column reboiler in the benzene separation column in the aromatics removal zone.

This arrangement minimizes the hot oil duty on the reboilers in both benzene separation columns. In one embodiment, it results in a reduction of duty about 15% for the benzene separation column in the alkylbenzene separation zone, and a reduction of duty of about 40% for the benzene separation column in the aromatics removal zone Furthermore, this flow scheme provides improved control of the entrance temperature to the aromatics removal zone during start-up and shutdown, when less duty can be transferred into the mid-reboilers.

In one embodiment, an n-paraffin stream is dehydrogenated to form a first dehydrogenated stream containing n-paraffins, mono-olefins, di-olefins, and aromatics. Heat is removed from at least a portion of the first dehydrogenated stream in a mid-column reboiler in a benzene separation column in an alkylbenzene separation zone to form a second dehydrogenated stream. The mid-column reboiler is positioned to obtain the maximum heat recovery while maintaining proper operation of the column. The temperature of the second dehydrogenated stream is lower than the temperature of the portion of the first dehydrogenated stream. The portion of the first dehydrogenated stream has a first temperature in the range of about 150° C. to about 250° C., and the temperature of the second dehydrogenated stream is in the range of about 135° C. to about 165° C.

Aromatics are removed from the second dehydrogenated stream in an aromatics removal zone forming an aromatics stream, a mono-olefin stream, and a first benzene stream. The aromatics removal zone includes at least one aromatics removal unit and a benzene separation column.

Benzene is alkylated with the mono-olefin stream in an alkylation zone. The alkylation effluent stream comprising alkylbenzene, benzene, and n-paraffins.

The alkylation effluent stream is separated into an alkylbenzene stream and a second benzene stream in the benzene separation column of the alkylbenzene separation zone.

In a preferred embodiment, before removing the aromatics from the second dehydrogenated stream, heat is removed from the second dehydrogenated stream in a mid-column reboiler in the benzene separation column in the aromatics removal zone to form a third dehydrogenated stream having a third temperature lower than the second temperature. In this case, the aromatics are removed from the third dehydrogenated stream. The mid-column reboiler is positioned such that the third temperature is in a range of about 110° C. to about 140° C.

Optionally, before removing the aromatics from the second dehydrogenated stream, additional heat can be removed from the third dehydrogenated stream in a heat exchanger using the benzene stream in the aromatics removal zone to form a fourth dehydrogenated stream having a fourth temperature lower than the third temperature. In this case, the aromatics are removed from the fourth dehydrogenated stream.

In a preferred embodiment, before removing heat from the portion of the first dehydrogenated stream, the first dehydrogenated stream is selectively hydrogenated to remove at least a portion of the di-olefins forming a selectively hydrogenated stream. The selectively hydrogenated stream is separated into a light ends stream and a bottoms stream. In this situation, the bottoms stream comprises the portion of the first dehydrogenated stream.

In a preferred embodiment, the alkylbenzene separation zone also includes a a benzene separation column and paraffin separation column. The alkylbenzene effluent is separated in the benzene separation column into a first alkylbenzene stream, which contains alkylbenzene and n-paraffins, and a benzene stream. The first alkylbenzene stream is then separated in the paraffin separation column into an n-paraffin stream and a second alkylbenzene stream. The n-paraffin stream can be recycled to the dehydrogenation zone.

In a further preferred embodiment, the alkylbenzene separation zone also include an alkylbenzene separation column. The second alkylbenzene stream is separated in the alkylbenzene separation column into a linear alkylbenzene stream and a heavy alkylate stream.

In a preferred embodiment, the aromatics removal zone includes at least two aromatics removal units. When there are at least two aromatics removal units, one or more can be in use, while one or more other units are being regenerated. In a preferred embodiment, there are at least two aromatics removal units operated in a swing bed arrangement.

Each aromatics removal unit can include one or more adsorption beds containing an adsorbent.

The n-paraffin rich stream can come from a variety of sources, including, but not limited to, adsorptive separation processes, and processes for making renewable feedstocks. By n-paraffin rich stream, we mean that the stream comprises at least about 50% n-paraffins, or at least about 55% n-paraffins, or at least about 60% n-paraffins, or at least about 65% n-paraffins, or at least about 70% n-paraffins, or at least about 75% n-paraffins, or at least about 80% n-paraffins, or at least about 85% n-paraffins, or at least about 90% n-paraffins, or at least about 95% n-paraffins, or at least about 96% n-paraffins, or at least about 97% n-paraffins.

In a preferred embodiment, the source of the n-paraffin stream is a kerosene feed stream. The kerosene feed stream is sent to a fractionation zone to form a fraction comprising hydrocarbons having between 10 and 13 carbon atoms. The C10-C13 fraction is hydrotreated, and the hydrotreated fraction is separated in an adsorptive separation zone to form the n-paraffin rich stream for the process and an isoparaffin rich stream.

In a preferred embodiment, the first benzene stream is recycled to the aromatics removal zone, or the second benzene stream is recycled to the alkylation zone, or both.

Figure 1:
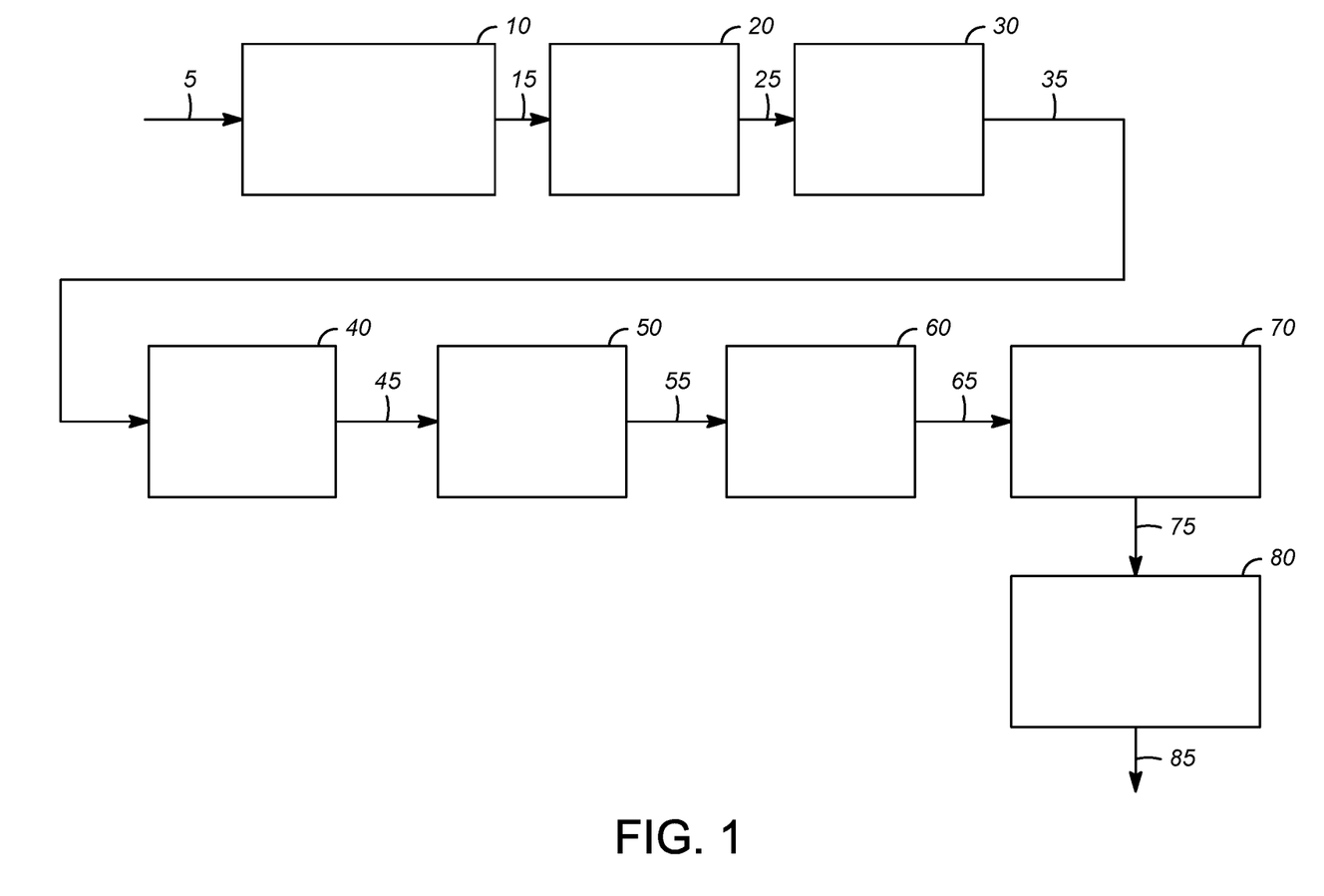
FIG. 1 is an illustration of one embodiment of an integrated process of making LAB from a kerosene feed.

For example, FIG. 1 illustrates an integrated process for producing linear alkylbenzene from a kerosene feed. The kerosene stream 5 is sent to a prefractionation zone 10 where it is separated into a fraction 15 comprising hydrocarbons having between 10 and 13 carbon atoms. The fraction 15 is sent to a hydrotreating zone 20 for hydrotreating. The hydrotreated stream 25 is sent to an adsorptive separation zone 30 where it is separated into an n-paraffin rich stream 35 and an iso-paraffin rich stream (not shown). The n-paraffin rich stream 35 is sent to a dehydrogenation zone 40 to form olefins. The dehydrogenation effluent 45 contains n-paraffins, mono-olefins, di-olefins, and aromatics. The dehydrogenation effluent 45 is sent to a selective hydrogenation zone 50 where the di-olefins are selectively hydrogenated to mono-olefins. A portion of the selectively hydrogenated effluent 55 is sent to an aromatics removal zone 60 where the aromatics are removed. The effluent 65 from the aromatics removal zone 60, which contains n-paraffins and mono-olefins, is sent to an alkylation zone 70 where benzene is alkylated with the mono-olefins to form alkylbenzene. The effluent 75 from the alkylation zone 70, which contains alkylbenzene, benzene, and n-paraffins, is sent to an alkylbenzene separation zone where the linear alkylbenzene product 85 is recovered.

Figure 2:
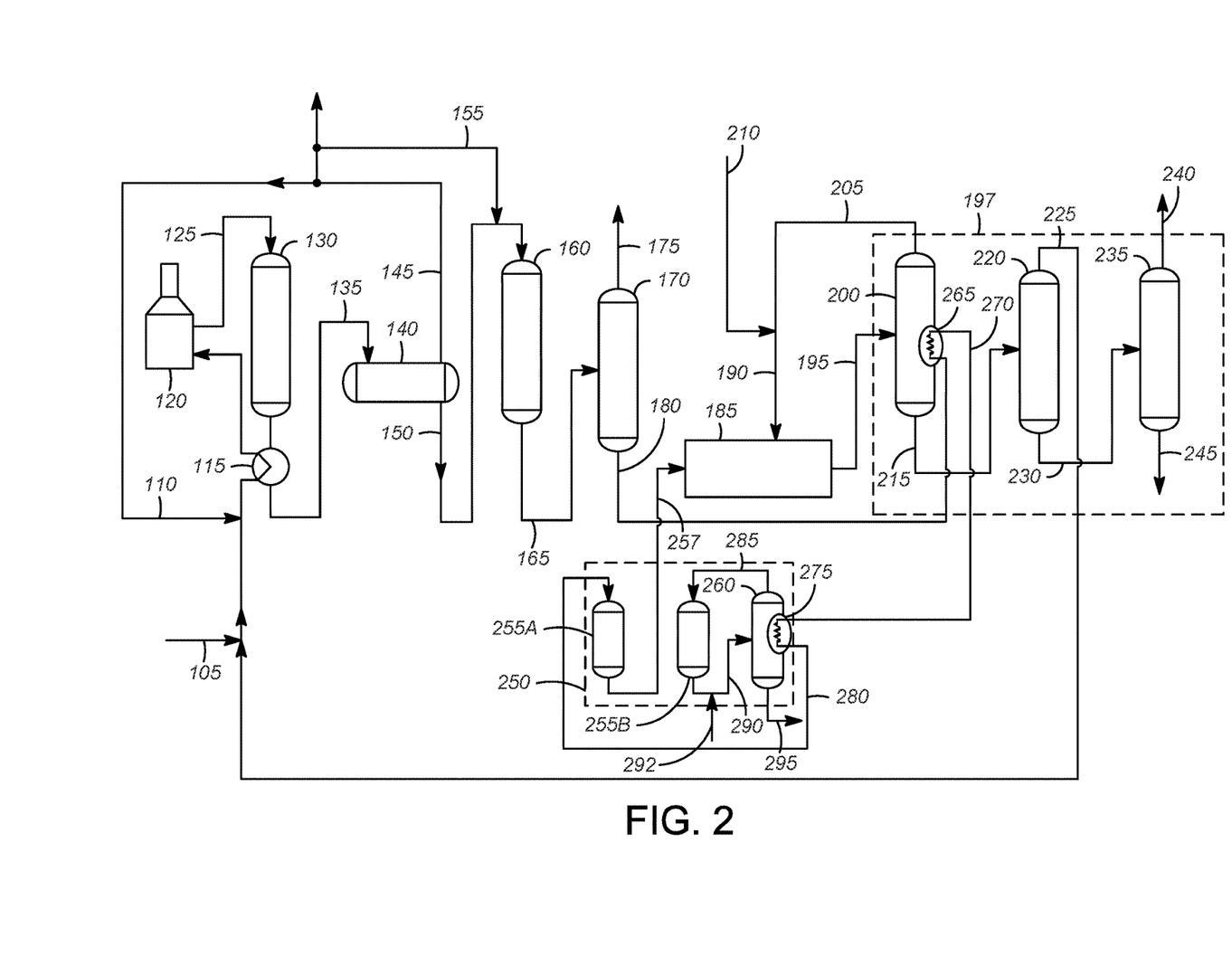
FIG. 2 is an illustration of a one embodiment of a portion of a process of making LAB.

FIG. 2 illustrates a portion of a process of making LAB in more detail. FIG. 2 includes a dehydrogenation process, followed by a selective catalytic hydrogenation process, an aromatics removal zone, an alkylation process, and an alkylbenzene separation process.

An n-paraffin rich feed 105 is mixed with hydrogen 110 and sent through heat exchanger 115 and charge heater 120.

The n-paraffin rich stream typically contains n-paraffins having 8 to 20 carbon atoms per molecule, or 8 to 18, or 8 to 17, or 8 to 15, or 8 to 13, or 10 to 13 carbon atoms per molecule. In order to make LAB, the n-paraffin rich stream desirably contains 10 to 13 carbon atoms per molecule.

The heated stream 125 is sent to dehydrogenation zone 130 where the paraffins are dehydrogenated into mono-olefins of the same carbon number as the paraffins. Typically, dehydrogenation occurs through known catalytic processes, such as the commercially popular Pacol process. Di-olefins and aromatics are also produced as undesired products of the dehydrogenation reactions.

Typical dehydrogenation conditions include a temperature in the range of about 420° C. to about 530° C., or about 460° C. to about 490° C., and a pressure in the range of about 90 kPa(g) to about 170 kPa(g), or about 110 kPa(g) to about 150 kPa(g). Any suitable dehydrogenation catalyst can be used. Generally, preferred suitable catalyst comprises a Group VIII noble metal component (e.g., platinum, iridium, rhodium, and palladium), an alkali metal component, and a porous inorganic carrier material. The catalyst may also contain promoter metals which advantageously improve the performance of the catalyst. The porous carrier material should be relatively refractory to the conditions utilized in the reactor section and may be chosen from those carrier materials which have traditionally been utilized in dual function hydrocarbon conversion catalysts. A preferred porous carrier material is a refractory inorganic oxide, with the most preferred an alumina carrier material.

The dehydrogenation effluent 135 exchanges heat with the n-paraffin rich feed 105 and hydrogen 110 in heat exchanger 115. The dehydrogenation effluent 135 is then sent to a separator 140 and separated into a hydrogen gas stream 145 and liquid stream 150, which contains unreacted n-paraffins, mono-olefins, and any di-olefins and aromatics formed in the dehydrogenation process.

The liquid stream 150 is mixed with hydrogen 155 and sent to a selective hydrogenation zone 160, such as a DeFine reactor, where at least a portion of the di-olefins are selectively hydrogenated to form mono-olefins. The effluent 165 from the selective hydrogenation zone 160 is sent to a stripper 170 where light ends 175, such as butane, propane, ethane, and methane that may have been formed from cracking or other reactions during the upstream processing, are removed.

Typical selective hydrogenation conditions include a temperature in the range of about 150° C. to about 250° C., or about 180° C. to about 220° C., and a pressure sufficient to maintain a liquid phase. Any suitable hydrogenation catalyst can be used, including but not limited to, a catalyst comprising nickel and sulfur dispersed on an alumina support material having a high surface area.

Bottoms stream 180 is sent to an aromatics removal zone 250. The temperature of bottoms stream 180 is typically in the range of about 150° C. to about 180° C. The temperature of the stream entering the aromatics removal zone 250 should be in the range of about 110° C. to about 140° C. Thus, the temperature of bottoms stream 180 must be reduced before it enters the aromatics removal zone 250. This is typically done currently with air or water cooling.

The present arrangement is designed to utilize as much of the excess heat in the bottoms stream 180 as possible, thereby minimizing the hot oil and cooling duties for benzene columns in the alkylbenzene separation zone 197 and the aromatics removal zone 250.

The aromatics removal zone 250 as shown includes two aromatics removal units 255A and 255B and a second benzene separation column 260. The aromatics removal zone 250 can include one or more aromatics removal units and one or more benzene separation columns 260. For example, there could be one or more aromatics units in use, one or more aromatics units in standby, and/or one or more units being regenerated.

As illustrated, aromatics removal unit 255A is in use, and aromatic removal unit 255B is being regenerated. The aromatics removal units 255A and 255B can be operated in a swing bed arrangement as is known in the art. The aromatics removal units 255A and 255B can be one or more adsorption beds containing adsorbent for removing aromatics.

Typical conditions for aromatics removal include a temperature in the range of about 80° C. to about 185° C., or about 100° C. to about 165° C., and a pressuresufficient to maintain a liquid phase. Typical adsorbent for aromatics removal include, but are not limited to, Na faujasite X zeolite.

Before being introduced into the aromatics removal zone 250, heat is removed from bottoms stream 180. Bottoms stream 180 is sent to a mid-column reboiler 265 in the first benzene separation column 200, which is part of the alkylbenzene separation zone 197. The location of the mid-column reboilers is designed to maximize the heat recovery from the hot stream while maintaining the operability of the column. Considerations include sizing of both the mid-column reboiler and the bottoms reboiler, as well as considerations for startup, turndown, etc. This is done using a process simulator, as is known in the art.

Heat is removed from the bottoms stream 180 resulting in the second bottoms stream 270 have a temperature less than the temperature of bottoms stream 180. The heat exchange of bottoms stream 180 with the mid-column reboiler 265 reduces the temperature of the second bottoms stream 270 to a temperature in the range of about 135° C. to about 165° C.

Second bottoms stream 270 may then be sent to a mid-column reboiler 275 in the second benzene separation column 260, which is part of the aromatics removal zone 250, to remove heat from second bottoms stream 270, resulting in third bottoms stream 280 which has a temperature less than second bottoms stream 270. The heat exchange of second bottoms stream 270 with the mid-column reboiler 275 reduces the temperature of third bottoms stream 280 to a temperature in the range of about 110° C. to about 140° C.

Third bottoms stream 280 is sent to the aromatics removal zone 250 where aromatics are removed by adsorption. The aromatics removal zone 250 as shown includes two aromatics removal units 255A and 255B and a second benzene separation column 260. As illustrated, aromatics removal unit 255A is in use, and aromatics removal unit 255B is being regenerated. The aromatics removal units 255A and 255B can be operated in a swing be arrangement as is known in the art. The aromatics removal units 255A and 255B can be adsorption units containing adsorbent for aromatics.

Third bottoms stream 280 is sent to aromatics removal unit 255A where the aromatics are adsorbed onto an adsorbent. Mono-olefins stream 257 from aromatics removal unit 255A, which contains mono-olefins and unreacted n-paraffins, is then sent to alkylation zone 185.

Aromatics removal unit 255B is regenerated with benzene stream 285 from the second benzene separation column 260. The benzene removes the adsorbed aromatics from the adsorbent in aromatics removal unit 255B. Effluent stream 290 contains benzene and aromatics. Effluent stream 290 is sent, along with benzene stream 292, to the second benzene separation column 260 where it is separated into benzene stream 285 and aromatics stream 295. Benzene stream 285 is recycled to aromatics removal unit 255B for regenerating the adsorbent bed. Aromatics stream 295 can be recovered. Aromatics stream 295 is typically used for fuel.

In some embodiments (not shown), an additional heat exchange step can be performed. If the temperature of the third bottoms stream 280 is not within the desired operating range of the aromatics removal unit 255A, third bottoms stream 280 can be cooled in an optional heat exchanger (not shown) with the benzene stream 285 from the second benzene separation column 260.

Mono-olefins stream 257 from the aromatics removal zone 250 is sent to the alkylation zone 185 where it is mixed with a benzene stream 190. The alkylation zone includes a catalyst that supports alkylation of the benzene with the mono-olefins forming alkylbenzene.

Typical alkylation conditions include a temperature in the range of about 80° C. to about 200° C., or about 100° C. to about 170° C., and a pressure in the range of about 1300 kPa(g) to about 1700 kPa(g), or about 2000 kPa(g) to about 3500 kPa(g). Typical alkylation catalysts include, but are not limited to, hydrogen fluoride, a sulfuric acid, a hydrofluoric acid, fluorosulfonic acids, a phosphoric acid, a metal halide (typically in conjunction with a Brönsted acid co-catalyst), solid catalysts, ionic liquids, or other suitable alkylation catalyst.

The effluent 195 from the alkylation zone 185 contains alkylbenzene and unreacted benzene, as well as paraffins. The effluent 195 is sent to an alkylbenzene separation zone 197. The alkylbenzene separation zone 197 can include one or more separation columns, including but not limited to, distillation columns, fractionation columns, and splitter columns. As illustrated, the alkylbenzene separation zone 197 includes a first benzene separation column 200, a paraffin separation column 220, and an alkylbenzene separation column 235.

The effluent 195 is sent to the first benzene separation column 200 where benzene is separated from the alkylbenzene. The benzene overhead stream 205 can be mixed with fresh benzene 210 to form the benzene stream 190.

The bottoms stream 215 from the first benzene separation column 200, which contains alkylbenzene and paraffins, is sent to a paraffin separation column 220 where the paraffins are separated from the alkylbenzene. The paraffin overhead stream 225 is mixed with n-paraffin rich feed 105 and sent to the dehydrogenation zone 130.

The bottoms stream 230 from the paraffin separation column 220, which contains alkylbenzene and heavy alkylate, is sent to an alkylbenzene separation column 235 where it is separated into an overhead stream 240 containing the alkylbenzene and a bottoms stream 245 containing heavy alkylate.

The overhead stream 240 can be further processed, for example, in a finishing column (not shown), if desired. The bottoms stream of heavy alkylates can be further processed, for example, in a transalkylation unit (not shown), to further enhance the yield of linear alkylbenzene, if desired.

In further detail for purposes of illustration, the benzene distillation is generally conducted with a bottoms temperature of less than about 300° C., preferably less than about 275° C., usually between about 230° C. and 270° C., and at a pressure at which the overhead is provided of between about 5 and 300, preferably between about 20 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays, but most often trays such as sieve and bubble trays, are used. Often the assembly provides at least about 5 theoretical plates, for example, 6 to 70, or 20 to 50. The reflux to feed ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux to feed ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene. The paraffins distillation may occur in a single column, or two or more distinct columns may be used.

The alkylbenzene distillation is generally conducted with a bottoms temperature of less than about 300° C., or less than about 275° C., usually between about 250° C. and 275° C., and at a pressure of between about 0.5 and 30 kPa absolute, or between about 1 and 5 kPa absolute. The column may contain any convenient packing or distillation trays, but most often structured packing is used. Often the alkylbenzene distillation provides at least about 5 theoretical plates, for example 10 to 30, or 10 to 20. The reflux ratio is often in the range of about 2:1 to 1:5, or about 0.2:1 to 1:1. The overhead from the alkylbenzene distillation generally contains less than about 1000, or less than about 100 ppmw, and sometimes less than about 50 ppmw, total heavies.

Example

For a 120 thousand metric ton per annum (KMTA) LAB complex, a comparison of column duties with and without mid-column reboilers was made.

|  | Parallel Columns | Parallel Columns w/ Midboilers |
|---|---|---|
| PEP Column Reboiler (MMkCal/hr) | 2.6 | 1.5 |
| New Benzene Column Reboiler (MMkCal/hr) | 6.4 | 5.4 |

The use of the mid-column reboiler in the benzene separation column in the alkylbenzene separation zone results in a 15% reduction in duty, while for the benzene separation column in the aromatics removal zone, the reduction in duty was 40%.

By about, we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a method of heat integration in a process for producing alkylbenzene comprising dehydrogenating an n-paraffin rich stream in a dehydrogenation zone under dehydrogenation conditions to form a first dehydrogenated stream comprising n-paraffins, mono-olefins, di-olefins, and aromatics, the dehydrogenated stream having a first temperature; removing heat from at least a portion of the first dehydrogenated stream in a mid-column reboiler in a first benzene separation column to form a second dehydrogenated stream, the portion of the first dehydrogenated stream having a first temperature in a range of about 150° C. to about 250° C., the second dehydrogenated stream having a second temperature lower than the first temperature, the mid-column reboiler positioned such that the second temperature is in a range of about 135° C. to about 165° C.; removing the aromatics from the second dehydrogenated stream in an aromatics removal zone to form an aromatics stream, a mono-olefin stream, and a first benzene stream, the aromatics removal zone comprising at least one aromatics removal unit and a second benzene separation column; alkylating benzene with the mono-olefin stream in an alkylation zone under alkylation conditions to provide an alkylation effluent stream comprising alkylbenzene, benzene, and n-paraffins; and separating the alkylation effluent stream into an alkylbenzene stream and a second benzene stream in an alkylbenzene separation zone comprising the first benzene separation column. An embodiment of the invention is one, any or all of prior embodiments in this paragraph up through the first embodiment in this paragraph further comprising removing heat from the second dehydrogenated stream in a mid-column reboiler in the second benzene separation column to form a third dehydrogenated stream having a third temperature lower than the second temperature before removing the aromatics from the second dehydrogenated stream, and wherein removing the aromatics from the second dehydrogenated stream comprises removing the aromatics from the third dehydrogenated stream, the mid-column reboiler positioned such that the third temperature is in a range of about 110° C. to about 140° C. An embodiment of the invention is one, any or all of prior embodiments in this paragraph up through the first embodiment in this paragraph further comprising removing heat from the third dehydrogenated stream in a heat exchanger using the first benzene stream to form a fourth dehydrogenated stream having a fourth temperature lower than the third temperature before removing the aromatics from the second dehydrogenated stream, and wherein removing the aromatics from the second dehydrogenated stream comprises removing the aromatics from the fourth dehydrogenated stream. An embodiment of the invention is one, any or all of prior embodiments in this paragraph up through the first embodiment in this paragraph further comprising selectively hydrogenating the first dehydrogenated stream to remove at least a portion of the di-olefins forming a selectively hydrogenated stream before removing heat from the portion of the first dehydrogenated stream; and separating the selectively hydrogenated stream into a light ends stream and a bottoms stream, wherein the bottoms stream comprises the portion of the first dehydrogenated stream. An embodiment of the invention is one, any or all of prior embodiments in this paragraph up through the first embodiment in this paragraph wherein the alkylbenzene separation zone further comprises a paraffin separation column, and wherein separating the alkylation effluent stream into the alkylbenzene stream and the second benzene stream comprises separating the alkylbenzene effluent into a first alkylbenzene stream and the second benzene stream in the first benzene separation column, wherein the first alkylbenzene stream comprises alkylbenzene and n-paraffins; separating the first alkylbenzene stream into an n-paraffin stream and a second alkylbenzene stream in the paraffin separation column; and recycling the n-paraffin stream to the dehydrogenation zone. An embodiment of the invention is one, any or all of prior embodiments in this paragraph up through the first embodiment in this paragraph wherein the alkylbenzene separation zone further comprises an alkylbenzene separation column, further comprising separating the second alkylbenzene stream in the alkylbenzene separation column into a linear alkylbenzene stream and a heavy alkylate stream. An embodiment of the invention is one, any or all of prior embodiments in this paragraph up through the first embodiment in this paragraph wherein the aromatics removal zone comprises at least two aromatics removal units. An embodiment of the invention is one, any or all of prior embodiments in this paragraph up through the first embodiment in this paragraph wherein one aromatics removal unit is regenerated with the first benzene stream while the second aromatics removal unit removes the aromatics from the second dehydrogenated stream. An embodiment of the invention is one, any or all of prior embodiments in this paragraph up through the first embodiment in this paragraph wherein the at least two aromatics removal units are in a swing bed arrangement. An embodiment of the invention is one, any or all of prior embodiments in this paragraph up through the first embodiment in this paragraph wherein the at least one aromatics removal unit comprises an adsorption bed. An embodiment of the invention is one, any or all of prior embodiments in this paragraph up through the first embodiment in this paragraph wherein the n-paraffin rich stream comprises an n-paraffin rich stream from an adsorptive separation process, or an n-paraffin rich stream produced from a renewable feedstock. An embodiment of the invention is one, any or all of prior embodiments in this paragraph up through the first embodiment in this paragraph further comprising introducing a kerosene feed stream into a fractionation zone to form a fraction comprising hydrocarbons having between 10 and 13 carbon atoms; hydrotreating the fraction; and separating the hydrotreated fraction in an adsorptive separation zone to form the n-paraffin rich stream and an isoparaffin rich stream. An embodiment of the invention is one, any or all of prior embodiments in this paragraph up through the first embodiment in this paragraph further comprising at least one of recycling the first benzene stream to the aromatics removal zone; and recycling the second benzene stream to the alkylation zone.

A second embodiment of the invention is a method of heat integration in a process for producing alkylbenzene comprising dehydrogenating an n-paraffin rich stream in a dehydrogenation zone under dehydrogenation conditions to form a first dehydrogenated stream comprising n-paraffins, mono-olefins, di-olefins, and aromatics, the dehydrogenated stream having a first temperature; removing heat from at least a portion of the first dehydrogenated stream in a mid-column reboiler in a first benzene separation column to form a second dehydrogenated stream, the portion of the first dehydrogenated stream having a first temperature in a range of about 150° C. to about 250° C., the second dehydrogenated stream, the second dehydrogenated stream having a second temperature lower than the first temperature, the second temperature being in a range of about 135° C. to about 165° C.; removing heat from the second dehydrogenated stream in a mid-column reboiler in a second benzene separation column to form a third dehydrogenated stream having a third temperature lower than the second temperature, the third temperature being in a range of about 110° C. to about 140° C.; removing the aromatics from the third dehydrogenated stream in an aromatics removal zone to form an aromatics stream, a mono-olefin stream, and a first benzene stream, the aromatics removal zone comprising at least one aromatics removal unit and the second benzene separation column; alkylating benzene with the mono-olefin stream in an alkylation zone under alkylation conditions to provide an alkylation effluent stream comprising alkylbenzene, benzene, and n-paraffins; separating the alkylation effluent stream into an alkylbenzene stream and a second benzene stream in an alkylbenzene separation zone comprising the first benzene separation column; recycling the first benzene stream to the aromatics removal zone; and recycling the second benzene stream to the alkylation zone. An embodiment of the invention is one, any or all of prior embodiments in this paragraph up through the second embodiment in this paragraph further comprising removing heat from the third dehydrogenated stream in a heat exchanger using the first benzene stream to form a fourth dehydrogenated stream having a fourth temperature lower than the third temperature before removing the aromatics from the third dehydrogenated stream, and wherein removing the aromatics from the third dehydrogenated stream comprises removing the aromatics from the fourth dehydrogenated stream. An embodiment of the invention is one, any or all of prior embodiments in this paragraph up through the second embodiment in this paragraph further comprising selectively hydrogenating the first dehydrogenated stream to remove at least a portion of the di-olefins forming a selectively hydrogenated stream before removing heat from the portion of the first dehydrogenated stream; and separating the selectively hydrogenated stream into a light ends stream and a bottoms stream, wherein the bottoms stream comprises the portion of the first dehydrogenated stream. An embodiment of the invention is one, any or all of prior embodiments in this paragraph up through the second embodiment in this paragraph wherein the alkylbenzene separation zone further comprises a paraffin separation column and an alkylbenzene separation column, and wherein separating the alkylation effluent stream into the alkylbenzene stream and the second benzene stream comprises separating the alkylbenzene effluent into a first alkylbenzene stream and the second benzene stream in the first benzene separation column, wherein the first alkylbenzene stream comprises alkylbenzene and n-paraffins; separating the first alkylbenzene stream into an n-paraffin stream and a second alkylbenzene stream in the paraffin separation column; separating the second alkylbenzene stream in the alkylbenzene separation column into a linear alkylbenzene stream and a heavy alkylate stream; and recycling the n-paraffin stream to the dehydrogenation zone. An embodiment of the invention is one, any or all of prior embodiments in this paragraph up through the second embodiment in this paragraph wherein the aromatics removal zone comprises at least two aromatics removal units, and wherein one aromatics removal unit is regenerated with the first benzene stream while the second aromatics removal unit removes the aromatics from the third dehydrogenated stream. An embodiment of the invention is one, any or all of prior embodiments in this paragraph up through the second embodiment in this paragraph wherein the at least one aromatics removal unit comprises an adsorption bed. An embodiment of the invention is one, any or all of prior embodiments in this paragraph up through the second embodiment in this paragraph wherein the n-paraffin rich stream comprises an n-paraffin rich stream from an adsorptive separation process, or an n-paraffin rich stream produced from a renewable feedstock.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A method of heat integration in a process for producing alkylbenzene comprising:
   dehydrogenating an n-paraffin rich stream in a dehydrogenation zone under dehydrogenation conditions to form a first dehydrogenated stream comprising n-paraffins, mono-olefins, di-olefins, and aromatics, the dehydrogenated stream having a first temperature;
   removing heat from at least a portion of the first dehydrogenated stream in a mid-column reboiler in a first benzene separation column to form a second dehydrogenated stream, the portion of the first dehydrogenated stream having a first temperature in a range of about 150° C. to about 250° C., the second dehydrogenated stream having a second temperature lower than the first temperature, the mid-column reboiler positioned such that the second temperature is in a range of about 135° C. to about 165° C.;
   removing the aromatics from the second dehydrogenated stream in an aromatics removal zone to form an aromatics stream, a mono-olefin stream, and a first benzene stream, the aromatics removal zone comprising at least one aromatics removal unit and a second benzene separation column;
   alkylating benzene with the mono-olefin stream in an alkylation zone under alkylation conditions to provide an alkylation effluent stream comprising alkylbenzene, benzene, and n-paraffins; and
   separating the alkylation effluent stream into an alkylbenzene stream and a second benzene stream in an alkylbenzene separation zone comprising the first benzene separation column.

2. The method of claim 1 further comprising:
   removing heat from the second dehydrogenated stream in a mid-column reboiler in the second benzene separation column to form a third dehydrogenated stream having a third temperature lower than the second temperature before removing the aromatics from the second dehydrogenated stream, and wherein removing the aromatics from the second dehydrogenated stream comprises removing the aromatics from the third dehydrogenated stream, the mid-column reboiler positioned such that the third temperature is in a range of about 110° C. to about 140° C.

3. The method of claim 2 further comprising:
removing heat from the third dehydrogenated stream in a heat exchanger using the first benzene stream to form a fourth dehydrogenated stream having a fourth temperature lower than the third temperature before removing the aromatics from the second dehydrogenated stream, and wherein removing the aromatics from the second dehydrogenated stream comprises removing the aromatics from the fourth dehydrogenated stream.

4. The method of claim 1 further comprising:
selectively hydrogenating the first dehydrogenated stream to remove at least a portion of the di-olefins forming a selectively hydrogenated stream before removing heat from the portion of the first dehydrogenated stream; and
separating the selectively hydrogenated stream into a light ends stream and a bottoms stream, wherein the bottoms stream comprises the portion of the first dehydrogenated stream.

5. The method of claim 1 wherein the alkylbenzene separation zone further comprises a paraffin separation column, and wherein separating the alkylation effluent stream into the alkylbenzene stream and the second benzene stream comprises:
separating the alkylbenzene effluent into a first alkylbenzene stream and the second benzene stream in the first benzene separation column, wherein the first alkylbenzene stream comprises alkylbenzene and n-paraffins;
separating the first alkylbenzene stream into an n-paraffin stream and a second alkylbenzene stream in the paraffin separation column; and
recycling the n-paraffin stream to the dehydrogenation zone.

6. The method of claim 5 wherein the alkylbenzene separation zone further comprises an alkylbenzene separation column, further comprising:
separating the second alkylbenzene stream in the alkylbenzene separation column into a linear alkylbenzene stream and a heavy alkylate stream.

7. The method of claim 1 wherein the aromatics removal zone comprises at least two aromatics removal units.

8. The method of claim 7 wherein one aromatics removal unit is regenerated with the first benzene stream while the second aromatics removal unit removes the aromatics from the second dehydrogenated stream.

9. The method of claim 7 wherein the at least two aromatics removal units are in a swing bed arrangement.

10. The method of claim 1 wherein the at least one aromatics removal unit comprises an adsorption bed.

11. The method of claim 1 wherein the n-paraffin rich stream comprises an n-paraffin rich stream from an adsorptive separation process, or an n-paraffin rich stream produced from a renewable feedstock.

12. The process of claim 1 further comprising:
introducing a kerosene feed stream into a fractionation zone to form a fraction comprising hydrocarbons having between 10 and 13 carbon atoms;
hydrotreating the fraction; and
separating the hydrotreated fraction in an adsorptive separation zone to form the n-paraffin rich stream and an isoparaffin rich stream.

13. The method of claim 1 further comprising at least one of:
recycling the first benzene stream to the aromatics removal zone; and
recycling the second benzene stream to the alkylation zone.

14. A method of heat integration in a process for producing alkylbenzene comprising:
dehydrogenating an n-paraffin rich stream in a dehydrogenation zone under dehydrogenation conditions to form a first dehydrogenated stream comprising n-paraffins, mono-olefins, di-olefins, and aromatics, the dehydrogenated stream having a first temperature;
removing heat from at least a portion of the first dehydrogenated stream in a mid-column reboiler in a first benzene separation column to form a second dehydrogenated stream, the portion of the first dehydrogenated stream having a first temperature in a range of about 150° C. to about 250° C., the second dehydrogenated stream, the second dehydrogenated stream having a second temperature lower than the first temperature, the second temperature being in a range of about 135° C. to about 165° C.;
removing heat from the second dehydrogenated stream in a mid-column reboiler in a second benzene separation column to form a third dehydrogenated stream having a third temperature lower than the second temperature, the third temperature being in a range of about 110° C. to about 140° C.;
removing the aromatics from the third dehydrogenated stream in an aromatics removal zone to form an aromatics stream, a mono-olefin stream, and a first benzene stream, the aromatics removal zone comprising at least one aromatics removal unit and the second benzene separation column;
alkylating benzene with the mono-olefin stream in an alkylation zone under alkylation conditions to provide an alkylation effluent stream comprising alkylbenzene, benzene, and n-paraffins;
separating the alkylation effluent stream into an alkylbenzene stream and a second benzene stream in an alkylbenzene separation zone comprising the first benzene separation column;
recycling the first benzene stream to the aromatics removal zone; and
recycling the second benzene stream to the alkylation zone.

15. The method of claim 14 further comprising:
removing heat from the third dehydrogenated stream in a heat exchanger using the first benzene stream to form a fourth dehydrogenated stream having a fourth temperature lower than the third temperature before removing the aromatics from the third dehydrogenated stream, and wherein removing the aromatics from the third dehydrogenated stream comprises removing the aromatics from the fourth dehydrogenated stream.

16. The method of claim 14 further comprising:
selectively hydrogenating the first dehydrogenated stream to remove at least a portion of the di-olefins forming a selectively hydrogenated stream before removing heat from the portion of the first dehydrogenated stream; and separating the selectively hydrogenated stream into a light ends stream and a bottoms stream, wherein the bottoms stream comprises the portion of the first dehydrogenated stream.

17. The method of claim 14 wherein the alkylbenzene separation zone further comprises a paraffin separation column and an alkylbenzene separation column, and wherein separating the alkylation effluent stream into the alkylbenzene stream and the second benzene stream comprises:

separating the alkylbenzene effluent into a first alkylbenzene stream and the second benzene stream in the first benzene separation column, wherein the first alkylbenzene stream comprises alkylbenzene and n-paraffins;

separating the first alkylbenzene stream into an n-paraffin stream and a second alkylbenzene stream in the paraffin separation column;

separating the second alkylbenzene stream in the alkylbenzene separation column into a linear alkylbenzene stream and a heavy alkylate stream; and recycling the n-paraffin stream to the dehydrogenation zone.

18. The method of claim 14 wherein the aromatics removal zone comprises at least two aromatics removal units, and wherein one aromatics removal unit is regenerated with the first benzene stream while the second aromatics removal unit removes the aromatics from the third dehydrogenated stream.

19. The method of claim 13 wherein the at least one aromatics removal unit comprises an adsorption bed.

20. The method of claim 13 wherein the n-paraffin rich stream comprises an n-paraffin rich stream from an adsorptive separation process, or an n-paraffin rich stream produced from a renewable feedstock.

* * * * *

UNITED STATES PATENT AND TRADEMARK OFFICE
CERTIFICATE OF CORRECTION

PATENT NO. : 10,131,591 B2
APPLICATION NO. : 15/857175
DATED : November 20, 2018
INVENTOR(S) : Nathan Siedler et al.

It is certified that error appears in the above-identified patent and that said Letters Patent is hereby corrected as shown below:

In the Claims

Claim 14, Lines 23 - 24, delete "the second dehydrogenated stream"

Signed and Sealed this
Twentieth Day of August, 2019

Andrei Iancu
*Director of the United States Patent and Trademark Office*